(12) United States Patent
Bowen et al.

(10) Patent No.: US 9,010,530 B2
(45) Date of Patent: Apr. 21, 2015

(54) SELF-ORIENTING DESICCANT HOLDER FOR USE WITH IN A SUCTION DEVICE

(71) Applicant: Synaptic Wireless, LLC, O'Fallon, MO (US)

(72) Inventors: Charles H. Bowen, O'Fallon, MO (US); P. Mark Bowen, Fayetteville, GA (US)

(73) Assignee: Synaptic Wireless, LLC, O'Fallon, MO (US)

( * ) Notice: Subject to any disclaimer, the term of this patent is extended or adjusted under 35 U.S.C. 154(b) by 0 days.

(21) Appl. No.: 13/797,053

(22) Filed: Mar. 12, 2013

(65) Prior Publication Data
US 2014/0144793 A1 May 29, 2014

Related U.S. Application Data

(60) Provisional application No. 61/730,381, filed on Nov. 27, 2012.

(51) Int. Cl.
*A61B 19/02* (2006.01)
*A61C 17/06* (2006.01)
*A61M 1/00* (2006.01)

(52) U.S. Cl.
CPC ............... *A61B 19/02* (2013.01); *A61C 17/043* (2013.01); *A61M 1/008* (2013.01); *A61B 19/0256* (2013.01)

(58) Field of Classification Search
CPC .................. A61B 19/0256; A61M 1/008
USPC .................. 206/210; 220/669; 433/77
See application file for complete search history.

(56) References Cited

U.S. PATENT DOCUMENTS

| | | | |
|---|---|---|---|
| 3,939,971 A * | 2/1976 | Tulis | 206/205 |
| 4,597,551 A | 7/1986 | Ciechanowski et al. | |
| 5,224,679 A | 7/1993 | Code | |
| 5,806,822 A | 9/1998 | Schulz | |
| 5,927,974 A | 7/1999 | Homra | |
| 6,077,074 A | 6/2000 | Homra | |
| D541,933 S | 5/2007 | White et al. | |
| 7,913,959 B2 | 3/2011 | White et al. | |
| 2005/0220666 A1* | 10/2005 | Foster | 422/28 |
| 2006/0229567 A1 | 10/2006 | Wright | |
| 2007/0199846 A1* | 8/2007 | Wright | 206/438 |
| 2009/0308823 A1 | 12/2009 | DiGasbarro | |

* cited by examiner

*Primary Examiner* — Anthony Stashick
*Assistant Examiner* — James Way
(74) *Attorney, Agent, or Firm* — Lewis Rice LLC (57) ABSTRACT

A receptacle for consistently orienting a sterilized surgical instrument for natural grasping by a physician without removing his or her vision from the operational field, wherein the receptacle may also comprise a reservoir and desiccant for maintaining sanitized or sterilized instruments.

16 Claims, 5 Drawing Sheets

SELF-ORIENTING DESICCANT HOLDER FOR USE WITH IN A SUCTION DEVICE

CROSS REFERENCE TO RELATED APPLICATION(S)

This application claims the benefit of U.S. Provisional Patent Application Ser. No. 61/730,381, filed Nov. 27, 2012, the entire disclosure of which is incorporated herein by reference.

BACKGROUND

1. Field of the Invention

This disclosure is related to the field of medical devices, specifically, receptacles for suction devices used in medical procedures.

2. Description of the Related Art

One of the most widely-used tools of the medical profession is a suction device. These devices commonly are used to clear airways of blood, saliva, vomit, and other secretions to improve breathing and pulmonary hygiene. Suction devices also commonly are used as surgical vacuums. In surgery, the patient tends to secrete blood and other biologically active fluids, which can be hazardous to the patient, physician, and attending staff, and inhibit the physician's view of the surgical field.

Figure 1A:
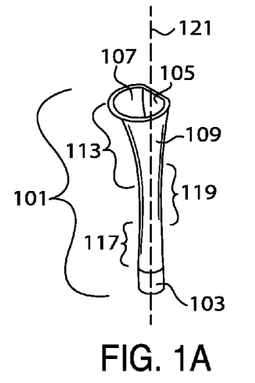
FIG. 1 provides various perspective views of an embodiment of a receptacle for a suction device.
Figure 1B:
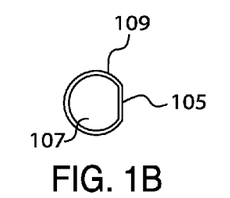
Figure 1C:
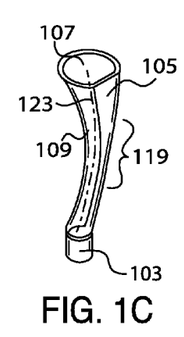
Figure 1D:
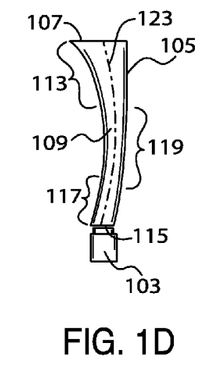
Figure 1E:
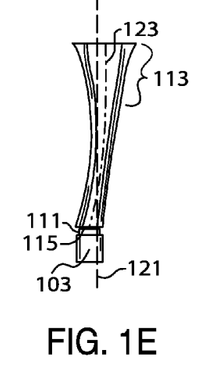
Figure 2:
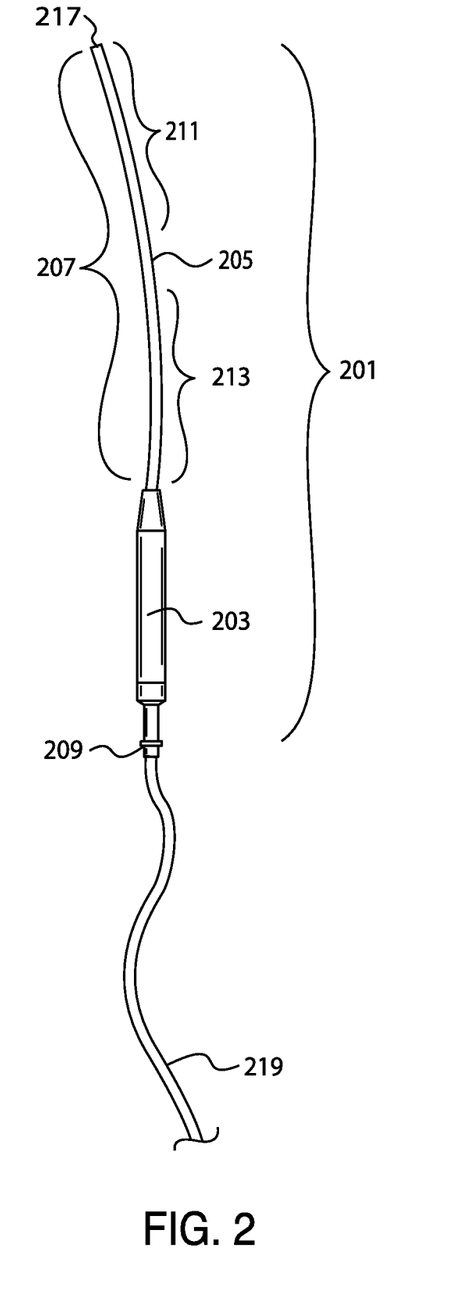
FIG. 2 provides an embodiment of a suction device.
Figure 3A:
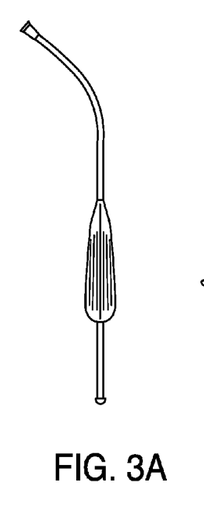
FIG. 3 provides multiple embodiments of suction devices.
Figure 3B:
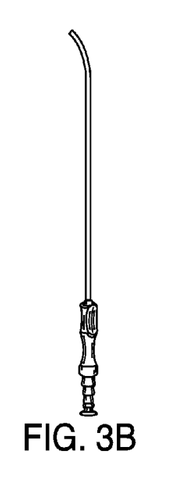
Figures 3C, 3D, 3E:
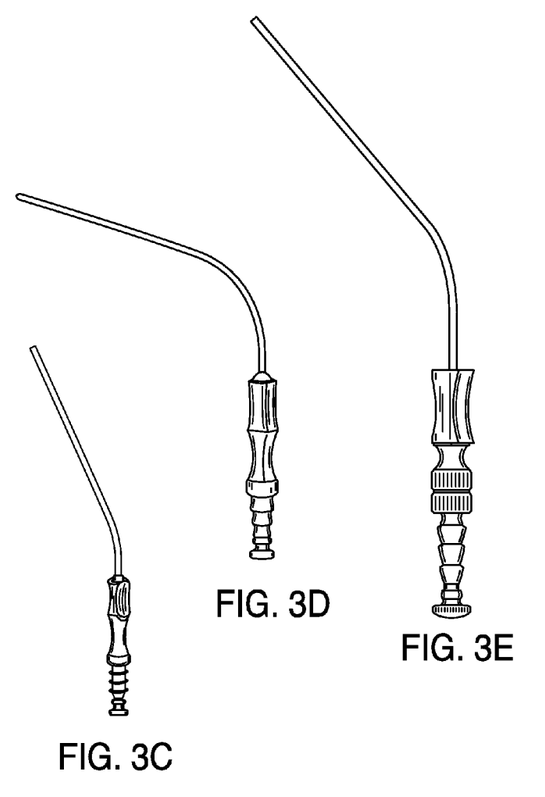

One of the most commonly used suction devices is a hand-held surgical vacuum. These devices generally comprise a handle (203) and an elongated, narrow wand (207), generally with a bend (205) for precise manipulation in the surgical field. Embodiments of such devices are depicted in FIGS. 2 and 3. The distal end (217) of the wand (207) has an opening for accepting biological matter. Suction usually is provided by a pump, and the device (201) is operated by the physician via a triggering mechanism, such as a lever or button on the handle (203) which turns the suction action on or off. Biological material is drawn into the open distal end (217) of the wand (207) and then deposited and isolated in a suitable storage container. Such containers may be directly attached to the device (201), or attached via tubing (219).

These suction devices are not without their flaws. For one, when the physician has finished using the device, the device must be stored in a safe, sterile location within reach of the physician, who often cannot safely remove his attention from the surgical field. Further, when the suction action is discontinued there may be biological matter which was drawn into the tube when the suction action was active, but which did not travel to the storage container before the physician discontinued the suction action. This material tends to collect in the wand and/or tubing unless, when the device is not in use, it is oriented with the open end facing downward so that gravity can pull out stray material. If the device is not properly oriented, this stray matter will tend to drain into the surgical field when the device next is used, risking contamination and infection to the patient, and further obscuring the physician's view.

However, if the device is placed in a manner which allows this drainage, the stray material simply accumulates on the floor of the operating room, or on another surface, contaminating the operating environment and presenting a slipping hazard. A storage container may be placed under the device to collect the leaked material, but as the material accumulates in the container over the course of a surgery, particularly a lengthy surgery, the level of the material in the container may become high enough that the material comes into contact with the tip of the suction device when the device is not in use. This also presents a risk of infection and contamination when the device is reinserted into the patient.

Further, in the sometimes fast-paced environment of an operating room, the container may be upended or dislodged, causing the collected material to discharge onto the environment, again contaminating the operating room and presenting a slipping hazard. These risks are further exacerbated where hospital staff forget to clean or replace the container, resulting in contamination of a sanitized device before surgery even begins.

Also, due to the shape and configuration of the suction device and the location of the controls on the handle, the device generally must be oriented in a specific position in order for the physician to use it properly. If the device is not properly oriented when the physician picks it up, then the physician must pause to reorient the device in-hand before using it. As often happens in surgery, the physician only has one hand available to perform this task because the other hand is in contact with the patient or is holding another device, and cannot safely be removed. The physician may attempt to reorient the device in his hand, but this is a delicate maneuver that itself poses a risk that the physician may drop the device, potentially contaminating the device environment, or other sterilized medical devices. In the fast-paced environment of a surgical procedure, particularly an emergency surgical procedure, the physician simply does not have time to reorient the handle of the suction device.

Further, the physician often may not safely look away from the patient without posing a risk to the patient. While this is sometimes solved by having attending staff pick up and orient the device for the physician, this still takes time and requires a manual transfer of the device from the nurse to the physician, which also poses a risk of droppage. The extra time required for the hand-off or re-orientation can take up precious seconds that the patient simply cannot spare, all while secretions continue to accumulate in the surgical field, further obscuring the physician's vision and posing a risk of infection to the patient.

Existing receptacles for suction devices suffer a number of deficiencies. First, many are "sided," meaning the suction device can only be inserted into the receptacle if placed in a particular manner to accommodate a right- or left-handed physician. This often means that when staff prepare the operating room, they select a receptacle with the wrong sidedness for the physician, which then must be discarded or re-sterilized, resulting in waste. However, universal receptacles—those without a built-in sidedness—do not automatically orient the suction device for comfortable grasping. Finally, receptacles generally require the physician to insert the suction device into the receptacle at a certain angle. This does not allow the physician to quickly drop the device into the receptacle without looking and still have the device properly oriented when the physician next uses it, but rather forces the physician to orient the device at the time of placement. This only exacerbates the foregoing problem that the physician often should not, or cannot, divert his attention from the surgical field.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, described herein, among other things is a receptacle for consistently orienting a sterilized surgical instrument for natural grasping by a physician without removing his or her vision from the operational field, wherein the receptacle may also comprise a reservoir and desiccant for maintaining sanitized or sterilized instruments.

Described herein, among other things, is a receptacle for a surgical vacuum, the receptacle comprising: a hollow curved tube having: an opposing top and bottom; a generally flat back truncating the tube lengthwise; a center axis, wherein the center axis is an at least two-dimensional curve defining the shape of the tube such that when a surgical vacuum is inserted into the tube through the open top the shape causes the vacuum when descending into the tube to come to rest with the handle of the vacuum oriented generally the same direction with respect the tube; and a reservoir attached to the bottom comprising a generally cylindrical hollow tube, wherein material draining from a surgical vacuum in the tube collects in the reservoir.

In an embodiment, the tube is flared near the top end.

In an embodiment, the tube is flared near the bottom end.

In an embodiment, the reservoir further includes a desiccant.

In an embodiment, the desiccant is a liquid.

In an embodiment, the desiccant is selected from the group consisting of silica gels, silica clay, vermiculite, desiccant paper, activated alumina, activated carbon, calcium oxide, zeolite, and calcium sulfate.

In an embodiment, the desiccant includes an anti-microbial agent selected from the group consisting of: an anti-viral agent, an anti-fungal agent, and an anti-bacterial agent.

In an embodiment, the tube is sanitized.

In an embodiment, the tube is sterilized.

In an embodiment, the center axis is a curve in three dimensions.

Also described herein, among other things, is a method for allowing a physician to grasp a surgical instrument without looking at the instrument, the method comprising the steps of: providing a receptacle for a surgical instrument comprising a generally hollow tube having opposing top and bottom sides and a center axis comprising an at least two-dimensional curve defining the shape of the tube such that when a surgical instrument is inserted into the tube through the open top the shape causes the instrument when descending into the tube to rotate; providing a sanitized surgical instrument having a handle; placing the receptacle within reach of a physician performing a surgical operation; the physician using the surgical instrument in the surgical operation; the physician placing the surgical instrument in the receptacle; the shape of the receptacle changing the orientation of the instrument in the receptacle such that when the instrument comes to rest in the receptacle, the handle is oriented for the physician to naturally grasp the handle without reorienting the handle; allowing the physician to grasp the surgical instrument without looking at the surgical instrument.

In an embodiment, the surgical instrument is a vacuum.

In an embodiment, the method further comprises: providing a receptacle further comprising a reservoir attached to the bottom comprising a generally cylindrical hollow tube; and collecting material draining from the surgical instrument in the reservoir.

In an embodiment, the method further comprises: providing a receptacle further comprising a desiccant in the reservoir; absorbing material draining from the surgical instrument into the reservoir with the desiccant.

In an embodiment, the desiccant is selected from the group consisting of silica gels, silica clay, vermiculite, desiccant papers, activated alumina, activated carbon, calcium oxide, zeolite, and calcium sulfate.

In an embodiment, the desiccant includes an anti-microbial agent selected from the group consisting of: an anti-viral agent, an anti-fungal agent, and an anti-bacterial agent.

In an embodiment, the desiccant includes metal ions.

In an embodiment, the receptacle is sanitized before the receptacle is placed within reach of the physician.

In an embodiment, the receptacle is sterilized before the receptacle is placed within reach of the physician.

DESCRIPTION OF THE PREFERRED EMBODIMENTS

Described herein, among other things, is a self-orienting desiccant holder for use with a suction device. The receptacle described herein is configured such that when a suction device is placed in the receptacle, the force of gravity will pull the device into a tube and rotate the suction device such that the orientation of the device with respect to the physician is consistent from use to use, allowing the physician to reliably place and grasp the handle in a usable orientation without taking his eyes from the surgical field or having to use two hands to reorient, or having to rely upon staff to orient the device for the physician. As described herein, the receptacle may further include a reservoir for isolating secretions and other biological active materials. Also as described herein, the receptacle may further include a desiccant system which reduces secretions egressing from the receptacle or reservoir, particularly in the event that the receptacle is dislodged and/or upended.

In the embodiment depicted in FIG. 1, the receptacle (101) generally includes a tube (109) and a reservoir (103). The depicted tube (109) is generally an elongated, hollow, and curved cylinder with one flattened back side portion (105). The top (113) and bottom (117) portions of the tube (109) are dilated or flared at the ends and tapering or narrowing toward the middle portion (119) of the tube (109), giving each end portion (113, 117) of the tube (109) a generally trumpet-shaped appearance. The tube (109) of FIG. 1 is generally in the shape of a curved cylinder, but is also offset in two axes or planes, having a slightly "twisted" appearance. This generally means that whereas the axis of a cylinder is a straight line, the axis (123) of the depicted tube (109) is a curve (123) in three-dimensional space. By way of example and not limitation, the curve of the tube axis (123) is distorted from a straight line along at least the y-axis when the tube (109) is viewed from the side, as depicted in FIG. 1. Similarly, the curve of the tube axis (123) is distorted from a straight line along at least the x-axis when the tube (109) is viewed from the front or back side, as depicted in FIG. 1.

These distortions in the tube axis (123) result in the characteristic "twisted" shape which encourages a suction device (201), when placed into the tube (109) and released, to rotate such that the device (201) is oriented in generally the same fashion with respect to the tube (109) each time the device (201) is placed and released into the tube (109).

Because of the curved tube axis (123) and tapering shape of the tube (109), certain surfaces of the suction device will come into contact with the interior wall of the tube (109) as the suction device (201) descends into the tube (109). If the device (201) is not properly oriented when deposited into the tube (109), further descent is unlikely unless the device (201) is rotated about its major lengthwise axis (121). Because the force of gravity exceeds the force of friction from contact with the interior surface of the tube (109), the device (201) will rotate appropriately to continue to descend into the tube (109), coming to rest at the same orientation with respect to the tube (109) each time the device (201) is placed into the tube (109) and released. Thus, the device (201) may be dropped into the tube (109) without looking, and at any angle or orientation, and the handle (203) will be oriented in the same manner for retrieval each time the device (201) comes to rest.

In the depicted embodiment, the flared top portion (113) has a generally circular top opening (107) allowing access to the hollow interior of the tube (109). Among other things, the top opening (107) is suitable for facilitating insertion of a suction device (201) into the hollow interior of the tube (109). In an embodiment, the physician places a suction device (201) into the receptacle (101) by inserting the tip (217) of the suction device (201) into the top opening (107) and lowering the wand (207) of the device (201) into the tube (109) until a sufficient portion of the wand (207) is within the tube (109) that, if the physician were to release the handle (203), the device (201) would descend further into the tube (109). In the depicted embodiment, the shape of the flared portions (113, 117) of the receptacle (101) and the curved tube axis (123) encourage this orientation of the device (201).

For example, the diameter of the tube (109) narrows from the top opening (107) to the middle portion (119) of the tube (109). As the wand (207) is lowered into the tube (109), the shape of the top flared portion (113) causes the suction device (201) increasingly to come into an alignment generally parallel with the lengthwise axis (121) of the tube (109), because the wand (207) cannot descend further into the narrowing tube (109) unless the device's (201) orientation with respect to the lengthwise axis (121) of the tube (109) becomes more parallel with the lengthwise axis (121). When the receptacle (101) is installed for use, the lengthwise axis (121) is also generally parallel to the pull of gravity. Thus, the center of gravity of the suction device (201) will tend to become increasingly centered over the top opening (107) as the wand (207) is lowered further into the tube (109), reaching a point at which the center of gravity is sufficiently above the top opening (107) that, if the device (201) is released, the pull of gravity will cause the device (201) to descend into the tube (109).

The flared top portion (113) also aids the physician in placing the device because, among other things, the shape results in a larger target into which the wand (207) may be inserted than if the top portion (113) were not flared. Because there is a larger opening (107), the tolerance for error by the physician when placing the device is larger, increasing the likelihood that the physician will successfully reseat the suction device (201) in the receptacle (101) without diverting his attention from the surgical field.

As depicted in FIGS. 2 and 3, medical suction devices (201) generally are in roughly a curved or squared "L-shape," having a narrow, elongated tubular wand (207) extending from a handle (203) with a curve or bend (205) at a particular angle and at a particular distance from the handle (203). The wand (207) thus comprises a portion that is straight (209) with respect to the handle (203), and a portion that is bent (211) at an angle with respect to the handle (203). The angle of this bend (205), the location of the bend (205) along the wand (207), and the sharpness of the bend (205) all may vary significantly with the particular suction device (201), as depicted in the embodiments of various suction devices (201) in FIG. 3.

Figure 4:
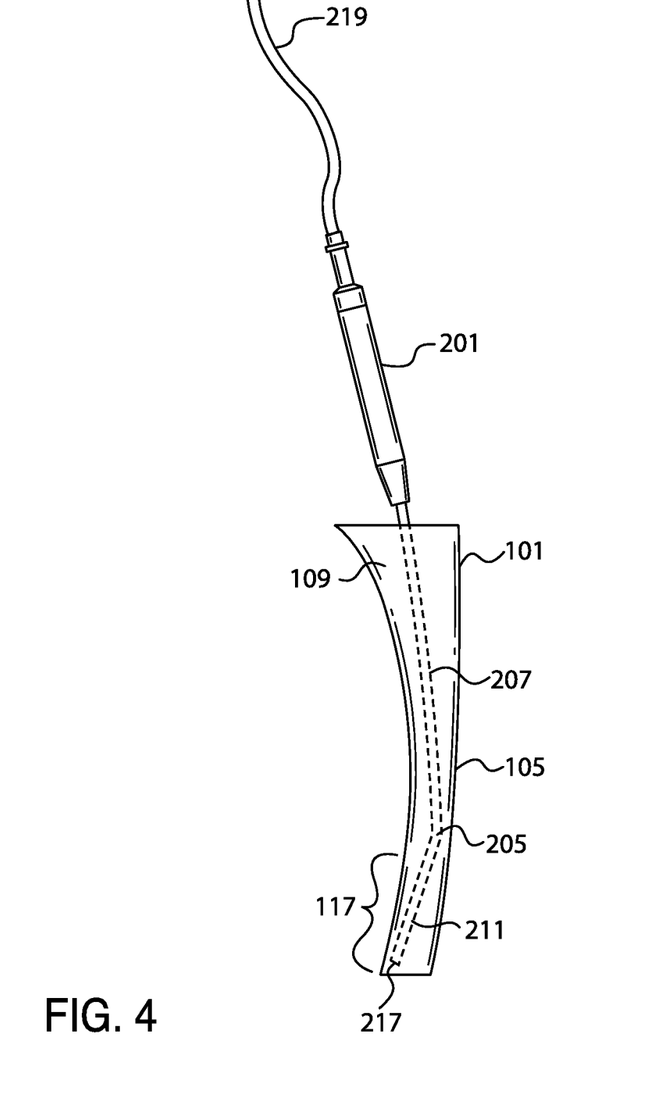
FIG. 4 provides a side perspective view of an embodiment of a suction device placed in an embodiment of a receptacle for a suction device.

For example, in the depicted embodiment of FIG. 4, the device (201) includes a bend (205) near the tip (217) of the wand, with a relatively short bent portion (211). In the depicted embodiment, the bottom portion (117) of the tube (109) is flared or dilated into a trumpet-shape. Among other things, this shape facilitates the aligning of the suction device (201) by accommodating the bent portion (211) of the wand (207), because the wand (207) fits best into the bottom flared portion (117) of the tube (109) if the bent portion (211) is turned in the direction of the flare rather than the flat back wall (105).

As elsewhere described herein, other facets of the shape and/or configuration of the receptacle (101) may facilitate rotation or orienting of the suction device (201). As described herein, the tube (109) of FIG. 1 is generally cylindrical but with a center axis (123) that is a curve in three-dimensional space, rather than a straight line. This shape, among other things, facilitates and encourages self-orientation of a suction device (201) placed in the tube (109). By way of example and not limitation, because the center axis (123) of the tube (109) is distorted from a straight line along at least the x-axis, the shape of the tube (109) is distorted from a cylinder along at least the x-axis. As a suction device (201) descends into the depicted tube (109), its orientation along the x-axis generally will change in correspondence with the distortion of the tube axis (123) along the x-axis. As the wand (207) is further lowered into the top portion (113), the tip (207) approaches the tapered, narrowed middle portion (119), further limiting the possible range of movement of the wand (207) within the tube (207) and encouraging the wand (207) to become oriented in correspondence with the curve of the tube axis (123) along the x-axis.

By way of example and not limitation, because the center axis (123) of the tube (109) is distorted from a straight line along at least the y-axis, the shape of the tube (109) is distorted from a cylinder along at least the y-axis. As a suction device (201) descends into the depicted tube (109), its orientation along the y-axis generally will change in correspondence with the distortion of the tube axis (123) along the y-axis. As the wand (207) is further lowered into the top portion (113), the tip (207) approaches the tapered, narrowed middle portion (119), further limiting the possible range of movement of the wand (207) within the tube (207) and encouraging the wand (207) to become oriented in correspondence with the curve of the tube axis (123) along the y-axis.

The distortion of the tube axis (123) in more than one dimension, among other things, orients the wand (207) such that when the pull of gravity does not cause the suction device (201) to descend any further into the tube (109), the orientation of the bent portion (211) of the wand (207) with respect to the x- and y-axis is generally the same each time the suction device (201) is placed into the tube (109), as depicted in FIG. 4. Because the construction of a suction device (201) is generally fixed such that the orientation of the bent portion (211)

relative to the handle (203) does not change, by facilitating generally consistent orientation of the bent portion (211) within the tube (109), the receptacle (101) also encourages generally consistent orientation of the handle (203) of the suction device (201). This in turn provides the physician a reliably- and predictably-oriented handle (203) for grasping the device (201), allowing the physician to grab the handle (203) without looking and having the device (201) properly oriented for use in the surgical field. This also allows the physician to reholster the device (201) in the receptacle (101) without removing his attention from the surgical field, and the receptacle (101) will properly orient the device (201) to the same angle for grasping by the physician each time the physician reholsters the device (201).

Figure 5:
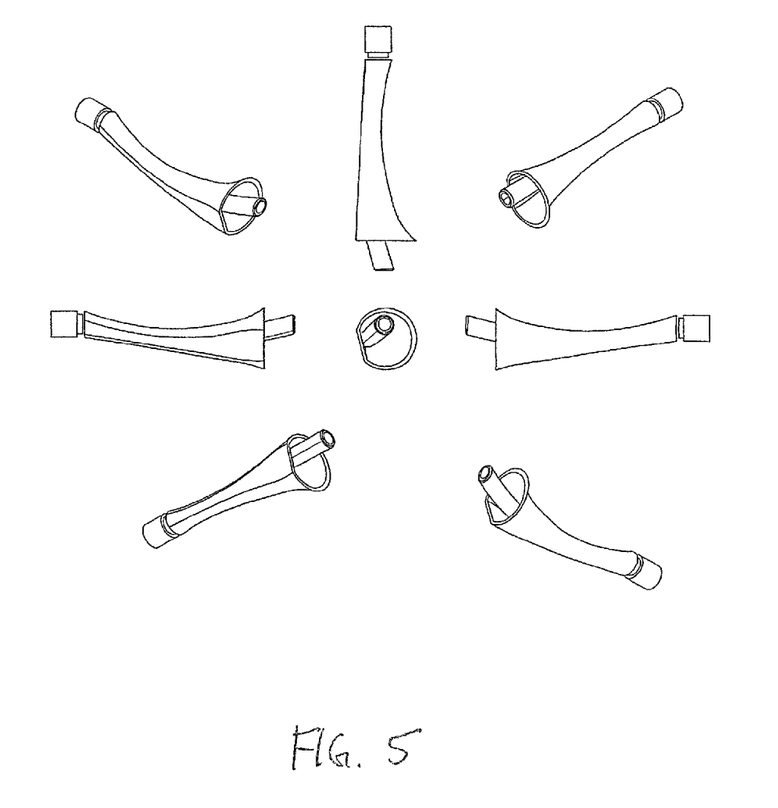
FIG. 5 provides multiple perspective views of an embodiment of a suction device placed in an embodiment of a receptacle for a suction device.

FIG. 5 depicts multiple perspective views of an alternate embodiment wherein a suction device is placed in an alternate embodiment of a receptacle for a suction device.

Component systems other than the shape of the tube (109) may be used to facilitate rotation. For example, in an embodiment, rotation is achieved by a set or series of ridges attached to the interior wall of the tube (109) which guide the device to the proper orientation. Although a tube (109) having generally circular cross-section with a flattened portion is depicted, the cross-section need not be circular. By way of example and not limitation, a tube (109) with a generally polygonal or ellipsoidal cross-section, or a combination thereof, is specifically contemplated.

When in use, the receptacle (101) is generally hung from or attached to a flat surface in the operating room, such as the side of a bed, gurney, or table, and oriented such that the lengthwise axis (121) of the tube (109) is generally parallel with the pull of gravity, and the top opening (107) faces upward to accept a suction device (201). When a suction device (201) is placed into the opening (207) and released, the pull of gravity will cause the device (201) to descend into the tube (109).

When the receptacle (101) is hung against a flat vertical surface, the round tube (109) may tend to roll along the flat surface, especially when bumped, potentially dislodging the suction device (201) or moving the receptacle (101) out of position. In the depicted embodiment of FIG. 1, the receptacle (101) includes a generally flat back side (105), giving the tube (109) a generally circular cross-section with a truncated arc. This flat back side (105), among other things, may reduce the susceptibility of the receptacle (101) to rolling or other undesired movement when bumped. Thus, when the receptacle (101) is installed, the flat back side (105) may be placed against a flat vertical surface to reduce the receptacle's (101) susceptibility to displacement when it, or the surface to which it is attached or hung, is jostled.

The receptacle (101) may be hung or installed through any suitable means. In an embodiment, the receptacle (101) includes a hanger (not depicted) which is part of or attachable to the receptacle (101). In an alternative embodiment, the receptacle (101) is installed through a means other than by hanging, such as by use of an adhesive. In such an embodiment, the flat back side (105), among other things, provides a suitable surface for applying an adhesive, as the amount of surface area of the flat back side (105) in contact with the gurney, bed, table, or other apparatus generally is greater than the surface area of the tube (109) in contact with such a surface, providing more adhesive to hold the receptacle (101) in place.

The shape of the tube (109), among other things, encourages material leaking from the tip (217) of the wand (207) to drain down the interior surface of the tube (109) toward the reservoir (103). Because the tip (217) is oriented, in the depicted embodiment of FIGS. 1 and 4, away from the flat back side (105) and toward the curved side of the tube (109), the leaked material is less likely to get caught or stuck in corners or creases, and more likely to drain toward the bottom of the tube (109), where it can be isolated by a desiccant system or reservoir (103). Because the interior of the tube (109) is generally sterile, the tip (217) may come into contact with the interior surface of the tube (109) without posing a significantly increased risk of infection or contamination to the patient.

The depicted embodiment of FIG. 1 further includes a system or method for isolating biologically active materials when and if they leak from the suction device (201), such as a reservoir (103). In the depicted embodiment of FIG. 1, the reservoir (103) is a generally cylindrical component having a diameter approximately the same as the diameter of the bottom opening (115) of the tube (109). In the depicted embodiment, the reservoir (103) includes a coupling portion (111) which is also generally cylindrical in shape, but shorter and squatter than the body of the reservoir (103), and the coupling component (111) is of generally the same diameter as the interior surface of the bottom opening (115). As such, in the depicted embodiment, the reservoir (103) can be attached to the tube (109) by inserting the coupling portion (111) into the bottom opening (115) of the tube (109). The resulting receptacle (101) then has the general appearance of a contiguous curved cylindrical shape, because the diameter of the reservoir body (103) is the same as the diameter of the tube at the bottom opening (115).

In an embodiment, the reservoir need not be configured to be the same diameter as any portion of the tube (109) but may be of any size and shape suitable for collecting and retaining biological secretions as contemplated and described herein. To secure the reservoir (103) to the tube (109), any suitable means for secure attachment is contemplated, such as but not limited to threaded components suitable for screwing or interlocking, a snap on design, friction or tension based mounting, adhesive, or other interlocking or intercoupling components suitable to hold the reservoir (103) in place against the tube (109). In an embodiment, the system for coupling the reservoir (103) to the tube (109) is temporary by design, so that the reservoir (103) may be quickly removed from the tube (109), such as but not limited to for replacement, repair, sterilization, cleaning, or examination.

In an embodiment, the reservoir (103) is detachable from the tube (109). This improves the cleaning or replacement or the reservoir (103). A detachable reservoir (103) may also be used to customize the configuration of a particular receptacle (101) for a particular operation. By way of example and not limitation, if the physician anticipates a lengthy operation involving a large volume of material, a large reservoir (103) may be attached to the tube (109). Among other things, it is easier for the physician or attending staff to identify whether a detachable reservoir (103) has been sterilized, cleaned, or soiled, prior to use.

In an embodiment having a detachable reservoir (103), where the reservoir (103) is disturbed, contaminated, cracked, defective, broken, or otherwise rendered unusable during a procedure, the detachable feature allows the unusable reservoir (103) to be quickly and easily replaced by a usable sterile reservoir (103) so that the receptacle (101) may continue to be used without significantly interrupting the procedure.

In an embodiment, the tube (109) and/or reservoir (103) include a system for isolating secretions. This system may be an absorbent material attached to the bottom of the reservoir (103) which soaks or isolates secretions. This material may be or contain antibacterial, antiviral and/or antifungal compounds to inhibit and/or prevent the growth of organisms or other compounds hazardous to the patient, the physician, the attending staff, or the surgical tools and materials.

In an embodiment, the system may include a second reservoir (not depicted) attached to the tube (109), such as by a sealed surgical tube attached to the bottom of the first reservoir (103). Secretions entering the first reservoir (103) would tend to be pulled into the tube by gravity, and to collect in the second reservoir, which generally has a larger volume and is safely located out of the way of the physician and attending staff. In such an embodiment, if the first reservoir (103) were to become dislodged or upended, a minimal amount of material would be discharged into the environment, reducing the risk of infection and/or contamination, as the majority of the material will have drained into the second reservoir and be isolated from the environment. In a still further embodiment, the tube (109) is itself attached directly to such a reservoir, such as via sealed surgical tube attached to the bottom of the tube (109).

In an embodiment, the system for isolating secretions is a desiccant system. The desiccant system may include a material or compound suitable for isolating secretions and other materials, and may be organic or inorganic. The desiccant system may include a loose material, such as but not limited to porous, granular, crystalline, or powdered materials, or in one or more solid absorbent forms, such as a stone or sponge. In an embodiment, the desiccant system includes a silica or sand. In an alternative embodiment, the desiccant system includes a sponge including a silica or sand. The desiccant system will generally include a largely dry material which is mostly chemically and biologically inert. By way of example and not limitation, such materials include silica gels and clays, vermiculite, fibrous desiccant materials, desiccant papers, activated alumina, activated carbon, calcium oxides, zeolite compounds, molecular sieves, calcium sulfate, and other anhydrous chemicals. In another embodiment, the desiccant may include a tape, film, or membrane. In a still further embodiment, the desiccant system includes a liquid desiccant. A desiccant system may also include additives which deactivate chemical or biological agents and/or contaminants, including but not limited to metal ions. A desiccant system may include anti-viral, anti-fungal, anti-bacterial, and anti-microbial compounds or chemicals. In an embodiment, the desiccant system includes a gel.

A desiccant material or system may be attached to an interior surface of the reservoir (103) or the tube (109) itself, or may be dispersed thereon. The desiccant system may itself be isolated, such as within a sachet, and distributed within the tube (109) or reservoir (103) prior to use. In an embodiment, the desiccant system may be temporarily secured to the reservoir (103), such as by an adhesive, and removed during cleaning and sterilization. In another embodiment, the tube (109) and/or reservoir (103) are disposable, and after the desiccant system is used or consumed, the entire receptacle (101) is discarded. In a still further embodiment, the desiccant system or material is laminated to a surface of the tube (109) or reservoir (103).

In an embodiment having a desiccant system, the desiccant system generally reduces the risk posed by dislodging or otherwise upsetting the receptacle (101). By way of example and not limitation, in an embodiment having a desiccant system including a silica or sand, when liquid secretions come into contact with the silica or sand, the liquid secretions will tend to be absorbed or adsorbed by the silica, and tend to become more viscous, or less liquid, or more solid. If the receptacle (101) is upset or dislodged, and the contents are discharged into the operating environment, the resulting spill may generally be more confined or easier to clean, because the desiccant system reduced the quantity or volume of liquid secretions, resulting in less liquid in the operating environment. Because liquids tend to run or flow across surfaces more so than solids, a lesser amount of liquid secretions may result in a more confined spill, consisting of less slippery material, reducing the risk of slips and falls which pose risk to the patient, physician, and staff. This may also reduce the likelihood of contamination or infection. Additionally, solid spills are generally easier to clean, and the surfaces are easier to sterilize, than liquid spills.

In an embodiment having a desiccant system, the desiccant system generally reduces the risk that the wand (207), specifically the open end (217), will come into contact with accumulated secretions. By way of example and not limitation, in an embodiment having a desiccant system including an absorbent material, by absorbing the liquid secretions, the level of such accumulated secretions in the reservoir (103) is lowered, meaning that when the wand (207) is inserted into the tube (109), the likelihood that the open end (217) of the wand (207) comes into contact with such secretions is lessened? Further, even if the wand (207) does come into contact with the absorbent materials of the desiccant system, there is less likelihood that secretions will become attached to the wand (207) than if the secretions were still in mostly liquid form.

In an embodiment, the systems and methods discourage egress of a desiccant system or a component system thereof. By way of example and not limitation, a desiccant system may include a sponge which, due to its shape and size, is too large to slip out of the tube (109) when the tube (109) is inverted. Also, by way of example and not limitation, this sponge may have a diameter generally the same as or greater than the bottom portion (117) of the tube (109). Because the tube (109) narrows or tapers from the bottom portion (117) to the middle portion (119), a sponge in such an embodiment would not be able to travel through the middle portion (119) of the tube (109), and thus could not egress through the top opening (107) and into the operating environment.

The receptacle (101) will generally be located near the surgical field, such as attached to the operating surface to one side of the physician, depending on the physician's handedness preference. In an embodiment, the tube (109) is configured such that the orientation of the suction device (201) when at rest in the tube (109) is suitable for easy grasping by either a right-handed or left-handed person. By way of example and not limitation, the receptacle (101) may be configured such that when a device (201) is at rest in the tube (109), the angle of the handle (203) relative to the surface to which the receptacle (101) is attached is generally perpendicular, resulting in generally the same angle with respect to either a right- or left-handed physician's hand.

In another embodiment, the tube (109) is configured such that the orientation of the suction device (201) at rest in the tube (109) is particularly suitable for easy grasping by a right- or left-handed person. By way of example and not limitation, the receptacle (101) may be configured such that when a device (201) is at rest in the tube (109), the handle (203) is angled toward the physician for particularly easily or comfortably grasping according to the physician's handedness preference.

It should be noted that the precise configuration of the tube (109) will depend on the particular suction device (201) with which the receptacle (101) is designed to be used. As depicted in FIG. 3, suction devices (201) are manufactured in a wide variety of sizes, shapes, lengths, triggering systems, pumping systems, secretion accumulation systems, and other options. For example, the direction and amount of curve in the tube axis (123) may vary depending on the suction device (201) for which the receptacle (101) is configured.

In an embodiment, the receptacle (101) is designed to self-orient a suction device (201) in which the suction is provided by a pump, but any system for providing suction may be used. For a pumping system, the system may be a squeeze-operated hand trigger, or a mechanical or electrical pump. The pump may be integrated into the suction device (201), or may be a device connected via tubing. In an embodiment, the receptacle (101) includes a notch or slot desired to accommodate a suction device (201) with attached tubing.

In an embodiment, the triggering system for the suction device (201) may be a button or lever, or squeeze trigger. Any triggering system is contemplated, and any location is contemplated, and the specific system and location may affect the design and configuration of the receptacle (101). For example, if the triggering system for a specific suction device (201) is a finger-operated squeeze lever that extends laterally from the handle (203), the receptacle (101) may include a notch or slot to allow gravity to pull the suction device (201) into the tube (109) and properly orient it without the squeeze lever getting caught on a lip or edge preventing the device (201) from descending into the tube (109). In another embodiment, where the device (201) does not include such a trigger, the tube (109) may not need such a notch or slot, through a receptacle (101) designed for use with multiple devices may nevertheless have one.

In an embodiment, the receptacle (101) is configured for use with a suction device (201) in which the handle (203) portion includes a reservoir. Such suction devices (201) are often mechanical and use a squeeze trigger to provide and activate the suction action, and biological material is then collected in a small reservoir attached directly to the device (201). In an embodiment, the receptacle (101) may include features or surfaces to accommodate the reservoir attached to the device (201) handle (203) while still permitting the device (201) to self-orient when placed in the tube (109).

In an embodiment, the receptacle (101) is configured for use with a device (201) that includes attachments such as replaceable wands (207) and extensions. In an embodiment, the receptacle (101) may itself be capable of accepting attachments which increase the distance between the tip (217) of the device (201) when at rest in the receptacle (101), and the reservoir (203). For example, the receptacle (101) may consist of two separable sections—a self-orienting section which accepts and orients a device (201), and a reservoir section, which may be of varying depth depending on whether, and which, extensions are attached to the suction device (201).

In an embodiment, the receptacle (101) is fashioned as a single monolithic piece of material. In another embodiment, the receptacle (101) is fashioned from multiple pieces of material attached together. Any method for attaching a receptacle (101) fashioned from multiple pieces of material is contemplated.

The receptacle (101) will most commonly be made of a generally translucent material suitable for use in a sterile environment. Such materials are easy to identify when soiled, easy to clean, easy to sanitize, and allow the physician and attending staff to quickly determine the level of material in the reservoir (103). Such materials include, without limitation, plastics and glasses. However, any material suitable for use in a sterile environment is contemplated, including without limitation opaque materials such as aluminum and stainless steel. An embodiment using an opaque material may also include a fluid level indicator system in the reservoir (103).

The interior surface of the receptacle (101) will generally be smooth to reduce the coefficient of friction of the surface and thus reduce the force of friction operating on the suction device (201) when released into the tube (109) so that the force of gravity will overcome the friction between the interior wall of the tube (109) and the device (201), and cause the device (201) to descend and rotate.

Because the tube (109) of the depicted embodiment causes the suction device (201) to descend only a certain distance into the tube (109) before coming to a rest, the tip (217) of the wand (207) does not generally come into contact with the bottom (115) of the tube (109). Thus, even though material collects in the reservoir (103), the material will not come into contact with the tip (217) of the wand (207), thus reducing the likelihood that the suction device (201) becomes contaminated. Further, in an embodiment having a desiccant system, the desiccant system will tend to absorb or otherwise reduce the amount or quantity of liquid secretions in the tube (109) or reservoir (103), further reducing the likelihood that the suction device (201) or a component thereof, will come into contact with biological secretions. This feature is particularly useful where staff neglect to replace or sterilize or otherwise clean the reservoir (103) following a procedure. When the receptacle (101) is used for the next procedure, biological material from the prior procedure has been absorbed, isolated and contained by the desiccant system, meaning that when a suction device (201) is inserted into the tube (209), that device (201) will not come in contact with the biological secretions from the prior patient.

While this invention has been disclosed in connection with certain preferred embodiments, this should not be taken as a limitation to all of the provided details. Modifications and variations of the described embodiments may be made without departing from the spirit and scope of this invention, and other embodiments should be understood to be encompassed in the present disclosure as would be understood by one of ordinary skill in the art.

The invention claimed is:

1. A receptacle for a surgical vacuum, said receptacle comprising:
   an elongated a hollow tube having:
      a center axis extending between an opposing open top end and open bottom end, said center axis defining a curve of said elongated hollow tube;
      a generally circular cross-section flared toward said top end and said bottom end such that said circular cross-section has a diameter greater at said open top end than at said open bottom end, and said circular cross-section has a diameter greater at said open bottom end than at a midpoint of said tube;
      a flat back truncating said cross-section lengthwise by forming a chord on said curve of said elongated hollow tube; and
   a reservoir removably attached to said open bottom end, said reservoir comprising a generally cylindrical hollow tube;
   wherein when a surgical vacuum is placed in said open top end of said receptacle, said surgical vacuum is suspended within said tube and does not extend into said reservoir.

2. The receptacle of claim 1, wherein said reservoir further includes a desiccant.

3. The receptacle of claim 2, wherein said desiccant is a liquid.

4. The receptacle of claim 2, wherein said desiccant is selected from the group consisting of silica gels, silica clay, vermiculite, desiccant paper, activated alumina, activated carbon, calcium oxide, zeolite, and calcium sulfate.

5. The receptacle of claim 2, wherein said desiccant includes an anti-microbial agent selected from the group consisting of: an anti-viral agent, an anti-fungal agent, and an anti-bacterial agent.

6. The receptacle of claim 1, wherein said tube is sanitized.

7. The receptacle of claim 1, wherein said tube is sterilized.

8. A method for orienting a surgical instrument during a surgical operation, said method comprising the steps of:
providing a receptacle for a surgical instrument comprising:
an elongated hollow tube having:
a center axis extending between opposing top and bottom ends and a center axis defining a curve of said elongated hollow tube;
a generally circular cross-section flared toward said top end and said bottom end such that said circular cross-section has a diameter greater at said open top end, than at said open bottom end, and said circular cross-section has a diameter greater at said open bottom end than at a midpoint of said tube;
a flat back truncating said cross-section lengthwise by forming a chord on said curve of said elongated hollow tube; and
a reservoir removably attached to said open bottom end; said reservoir comprising a generally cylindrical hollow tube;
providing a sanitized surgical instrument having a handle;
placing said receptacle adjacent a surgical operation;
placing said surgical instrument in said receptacle during said surgical operation using a plurality of different orientations said shape of said receptacle changing the orientation of said instrument in said receptacle such that when said instrument comes to rest in said receptacle, said handle is repeatedly oriented in a common orientation.

9. The method of claim 8, wherein said surgical instrument is a vacuum.

10. The method of claim 8, said method further comprising:
collecting material draining from said surgical instrument in said reservoir.

11. The method of claim 10, said method further comprising:
having a desiccant in said reservoir; and
absorbing material draining from said surgical instrument into said reservoir with said desiccant.

12. The method of claim 11, wherein said desiccant is selected from the group consisting of silica gels, silica clay, vermiculite, desiccant papers, activated alumina, activated carbon, calcium oxide, zeolite, and calcium sulfate.

13. The method of claim 11, wherein said desiccant includes an anti-microbial agent selected from the group consisting of: an anti-viral agent, an anti-fungal agent, and an anti-bacterial agent.

14. The method of claim 11, wherein said desiccant includes metal ions.

15. The method of claim 8, wherein said receptacle is sanitized before said receptacle is placed adjacent said surgical operation.

16. The method of claim 8, wherein said receptacle is sterilized before said receptacle is placed adjacent said surgical operation.

* * * * *